United States Patent
Xie et al.

(10) Patent No.: US 6,843,652 B2
(45) Date of Patent: Jan. 18, 2005

(54) SINGLE DOSE DENTAL IMPRESSION MATERIAL DELIVERY SYSTEM AND METHOD

(75) Inventors: Xiaoyi Xie, Diamond Bar, CA (US); Cynthia H. Kuess, Newport Beach, CA (US)

(73) Assignee: Kerr Corporation, Orange, CA (US)

( * ) Notice: Subject to any disclaimer, the term of this patent is extended or adjusted under 35 U.S.C. 154(b) by 0 days.

(21) Appl. No.: 10/313,567

(22) Filed: Dec. 6, 2002

(65) Prior Publication Data

US 2004/0110112 A1 Jun. 10, 2004

(51) Int. Cl.[7] .............................................. A61C 5/04
(52) U.S. Cl. ........................................ 433/90; 433/48
(58) Field of Search .............................. 433/48, 89, 90, 433/214; 222/575, 137

(56) References Cited

U.S. PATENT DOCUMENTS

| | | | |
|---|---|---|---|
| 4,753,536 A | 6/1988 | Spehar et al. | 366/339 |
| 4,995,540 A | 2/1991 | Colin et al. | 222/132 |
| 5,033,650 A * | 7/1991 | Colin et al. | 222/137 |
| 5,624,260 A | 4/1997 | Wilcox et al. | 433/90 |
| 5,722,829 A | 3/1998 | Wilcox et al. | 433/90 |
| 5,755,362 A * | 5/1998 | Rodriguez, Jr. et al. | 222/391 |
| 5,947,278 A | 9/1999 | Sawhney et al. | 206/216 |
| 6,201,038 B1 | 3/2001 | Waller et al. | 523/109 |
| 6,394,314 B1 | 5/2002 | Sawhney et al. | 222/137 |
| 6,547,101 B1 * | 4/2003 | Sogaro | 222/137 |

OTHER PUBLICATIONS

Sogaro, *Ampoule for Dispensing a Substance or a Mixture of a Plurality of Substances*, US 2002/0052579 A1, Publication Date May 2, 2002, Filed Oct. 31, 2001.

* cited by examiner

Primary Examiner—Cary E. O'Connor
(74) Attorney, Agent, or Firm—Wood, Herron & Evans, LLP

(57) ABSTRACT

A delivery system for supplying a single dose quantity of dental impression material. The system includes a dispenser having first and second chambers sized to contain first and second components of the single dose of dental impression material. The chambers are sealed by a closure that is movable from a sealed position to permit dispensing of the components through a mixing tip. The resulting dental impression material may be applied directly to a patient's dental anatomy and/or to a dental tray.

14 Claims, 2 Drawing Sheets

SINGLE DOSE DENTAL IMPRESSION MATERIAL DELIVERY SYSTEM AND METHOD

FIELD OF THE INVENTION

The present invention relates to dental materials, and more particularly to a single dose dental impression material delivery system.

BACKGROUND OF THE INVENTION

The use of elastomeric materials for obtaining dental impressions is well known in the art. Dental impressions are useful for providing detail of a patient's dental anatomy for the creation of inlays, onlays, full crowns and bridges, as well as removable prosthetic devices. Typically, the materials used to obtain dental impressions comprise two components. A low viscosity material is generally applied directly to the teeth, using for example, a syringe, and a separate higher viscosity material is placed into a dental tray for subsequent application to the teeth by inserting the tray into the patient's mouth and having the patient bite onto the tray. To obtain an optimum impression, it is important that the low viscosity material exhibit sufficient flowability to conform to the detail of the patient's dental anatomy while having sufficient viscosity to avoid spillage of the material off of the teeth and into the patient's mouth.

Prior methods of supplying and applying dental impression material have several drawbacks. According to one conventional method, impression materials are provided in separate containers to be measured and mixed by hand. The high viscosity and low viscosity materials are separately prepared and applied to the patient's teeth. This method of providing dental impression material is very time consuming and is prone to inaccurate mixing and/or measuring of the component materials, as well as exposure of the materials to contamination.

U.S. Pat. No. 4,995,540 to Colin et al. discloses a unit dosage dispenser for dental impression materials wherein the high and low viscosity materials are dispensed from a syringe-type device. The materials are provided in such a way that the low viscosity material is dispensed from the device first, followed by the high viscosity material. While this device addresses some concerns associated with the hand mixing of dental impression materials, it suffers drawbacks related to the timing of dispensing and applying the high and low viscosity materials from the device. For example, because the materials are contained in a common dispenser, they must be dispensed relatively contemporaneously with one another. The temporal dependence of dispensing the two materials may create problems when the set time or work time of the materials are not closely matched. Moreover, all of the low viscosity material must be dispensed before the high viscosity material may be applied to a dental tray.

There is thus a need for a dental impression material delivery system which overcomes drawbacks of the prior art, such as those described above.

SUMMARY OF THE INVENTION

The present invention provides a delivery system for supplying a single dose quantity of a two-component dental impression material. The delivery system includes a dispenser that maintains each component of the dental impression material in separate, sealed chambers until it is desired to dispense the impression material. The chambers are sealed by a closure which is moved from a sealed position to an unsealed position upon engagement with a dispensing tip. The dispenser thus provides a convenient and clean system for delivering the dental impression material to a desired target.

In another aspect of the invention, the first and second components of the dental impression material are base and catalyst materials, each having a viscosity in the range of approximately 1–200 Pa-s whereby the components may be easily dispensed in the syringe-type dispenser. In another aspect, the combined materials produce a desirable dental impression material having a viscosity in the range of approximately 20–2,000 Pa-s. Advantageously, the impression material may be applied directly to a patient's dental anatomy and used in a dental tray.

In another aspect of the invention, the impression material resulting from the combined first and second components is thixotropic. Accordingly, the dental impression material easily flows onto the patient's dental anatomy when dispensed, and readily forms an impression so as to not leak from the dental anatomy and into the patient's mouth. In yet another aspect of the invention, the impression material has a yield stress of approximately 0.5 Pa to approximately 100 Pa, whereby the material may be readily mixed in a short static mixer that is convenient to manipulate and which minimizes waste of the component materials.

In another aspect of the invention, a method of creating a dental impression comprises dispensing a dental impression material to the dental anatomy of a patient from a dispenser containing a base material and a catalyst material in a 1:1 ratio.

The features and objectives of the present invention will become more readily apparent from the following Detailed Description taken in conjunction with the accompanying drawings.

BRIEF DESCRIPTION OF THE DRAWINGS

The accompanying drawings, which are incorporated in and constitute a part of this specification, illustrate embodiments of the invention and, together with a general description of the invention given above, and the detailed description given below, serve to explain the invention.

DETAILED DESCRIPTION

Figure 1:
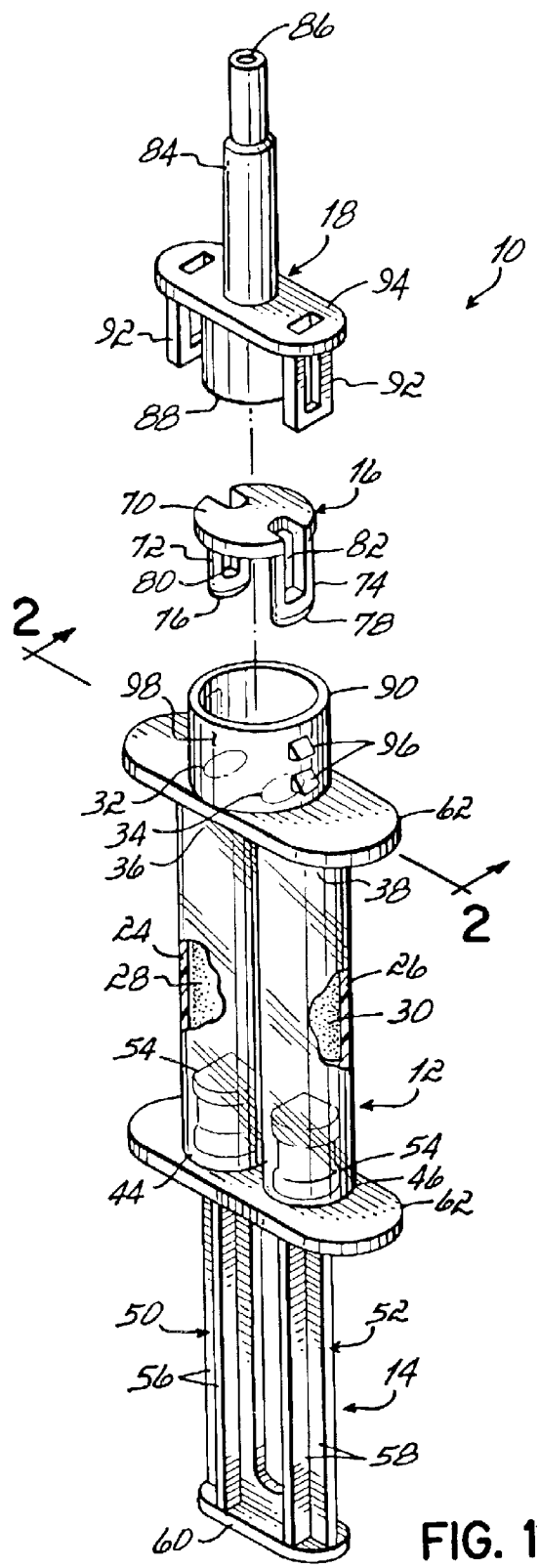
FIG. 1 is an exploded perspective view of an exemplary dispenser of the present invention.
Figure 2:
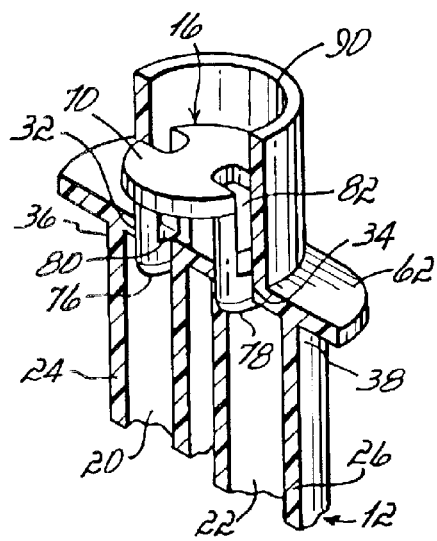
FIG. 2 is a partial cross-sectional view of the dispenser of FIG. 1 taken along lines 2—2.
Figure 3:
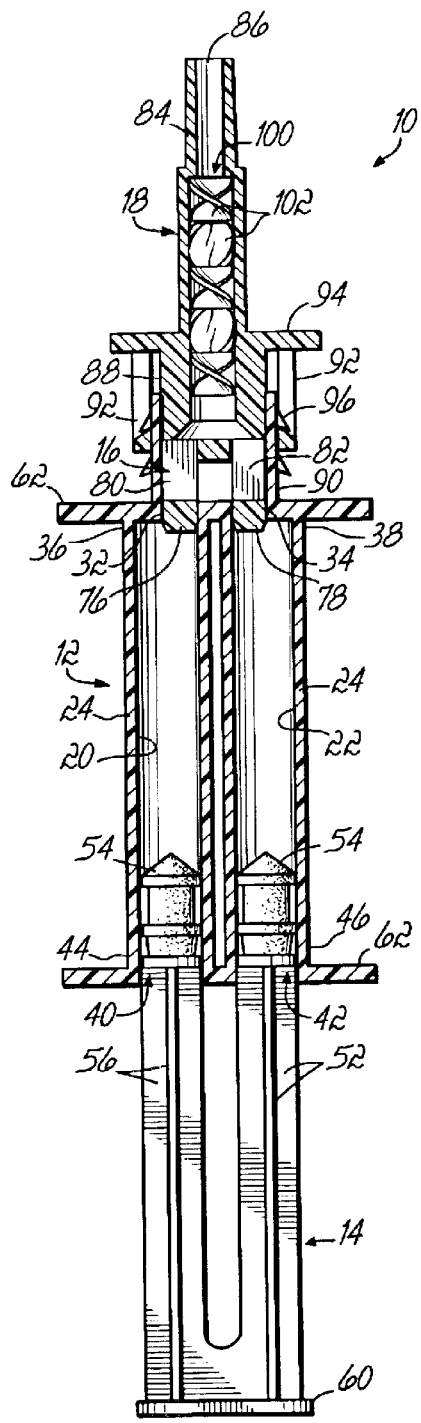
FIG. 3 is a cross-sectional view of the dispenser of FIG. 1 depicting the dispenser tip being attached.

Referring to FIGS. 1–4, there is shown an exemplary dispenser 10 for dispensing a single dose of a two component dental impression material according to the present invention. The dispenser 10 includes a dispenser body 12, an actuator 14, a closure 16, and a dispenser tip 18. With reference to FIGS. 1 and 3, the dispenser body 12 includes first and second cylindrically-shaped chambers 20, 22 defined by sidewalls 24, 26 and sized to contain the first and second components 28, 30 of the dental impression material. The first and second chambers 20, 22 are positioned adjacent one another and have dispensing orifices 32, 34 disposed at first ends 36, 38 of the chambers 20, 22 and openings 40, 42 at second ends 44, 46 of the chambers 20, 22 opposite the first ends 36, 38. The openings 40, 42 are sized to receive the actuator 14 which may thereafter be depressed into the chambers 20, 22 to dispense the first and second components 28, 30 of the dental impression material through the first and second orifices 32, 34, respectively.

The actuator 14 includes first and second plungers 50, 52 which may be received into the first and second chambers 20, 22, respectively, through their respective openings 40, 42. Each plunger 50, 52 includes a piston 54 which may be disposed within the respective chambers 20, 22 and is constructed to slidably seal against the sidewalls 24, 26 of the respective chambers 20, 22. The plungers 50, 52 further include elongated plunger rods 56, 58 which are configured to extend from the respective chambers 20, 22 through the openings 40, 42 whereby the pistons 54 may be urged along the respective chambers 20, 22 to dispense the respective dental impression material components 28, 30 as the respective plunger rods 56, 58 are depressed. In the exemplary embodiment shown, the first and second plungers 50, 52 are connected at their distal ends, opposite the pistons 54, by a thumb pad 60, whereby the pistons 54 may be advanced in unison along the chambers 20, 22 to dispense the first and second components 28, 30 simultaneously. The dispenser body 12 may further include one or more outwardly extending flanges 62 to provide a convenient means to grasp the dispenser 10 and to facilitate depressing the plungers 50, 52 of the actuator 14 into the chambers 20, 22 to dispense the components 28, 30.

Figure 4:
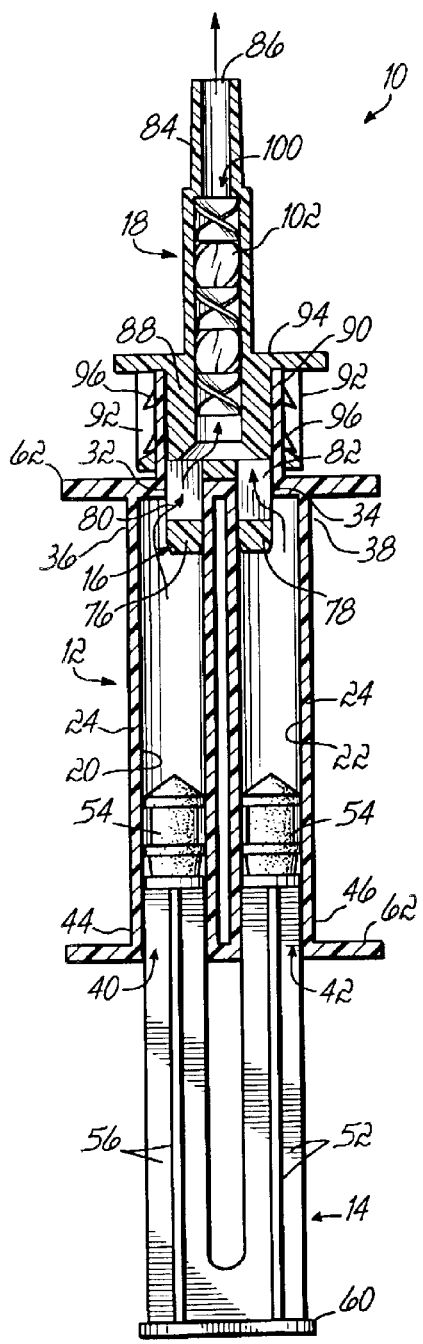
FIG. 4 is a cross-sectional view similar to FIG. 3 depicting the dispenser tip fully attached.

The dispenser 10 further includes a closure 16 which may be installed to the dispenser body 12 to seal the first and second orifices 32, 34. Advantageously, the closure 16 prevents premature dispensing of the dental impression components 28, 30 and protects the components 28, 30 from contaminants prior to use. In the exemplary embodiment shown, the closure 16 includes a disc-shaped base 70 having first and second projections 72, 74 extending from one side of the base 70. Sealing members 76, 78 are formed on the distal ends of the projections 72, 74 opposite the base 70 and are configured to sealingly engage the first and second orifices to thereby seal the first and second chambers 20, 22 when the closure 16 is attached to the dispenser body 12 adjacent the first and second orifices 32, 34 in a first position, as depicted in FIGS. 2 and 3. The closure 16 further includes slot-shaped passages 80, 82 formed between the sealing members 76, 78 and the base 70. These passages 80, 82 provide a path for the components 28, 30 to flow through the orifices 32, 34 when the closure 16 is moved from the first position to a second position, as depicted in FIG. 4, where the sealing members 76, 78 of the closure 16 are moved into the first and second chambers 20, 22, generally in a direction toward the first and second openings 40, 42.

Accordingly, the dispenser 10 may be placed into a condition for dispensing the first and second components 28, 30 by moving the closure 16 from the first position to the second position.

The dispenser 10 further includes a dispenser tip 18 which may be attached to the dispenser body 12 adjacent the first and second orifices 32, 34. In the exemplary embodiment shown, the dispenser tip 18 includes an elongate, cylindrically-shaped nozzle 84 having a nozzle outlet 86 through which the combined first and second components 28, 30 may be dispensed to a desired target area. The dispenser tip 18 further includes a cylindrically-shaped protrusion 88 at an end of the dispenser tip 18 opposite the nozzle 84. The protrusion 88 is sized to be received within a corresponding cylindrically-shaped extension 90 of the dispenser body 12, located adjacent the first and second orifices 32, 34. Advantageously, the protrusion 88 on the dispenser tip 18 and the extension 90 on the dispenser body 12 help to align and secure the dispenser tip 18 to the dispenser body 12 so that the first and second components 28, 30 flowing from the first and second orifices 32, 34 may be received into the dispenser tip 18 and dispensed through the nozzle 84.

The dispenser tip 18 may further include one or more hasps 92 provided on a flange 94 of the dispenser tip 18 and extending adjacent the cylindrical protrusion 88. The hasps 92 are configured to engage corresponding tabs 96 provided on an outer surface 98 of the cylindrical extension 90 on the dispenser body 12 whereby the hasps 92 may engage the tabs 96 in an interlocking relationship to secure the dispenser tip 18 to the dispenser body 12.

Advantageously, the cylindrical protrusion 88 on the dispenser tip 18 may be configured to engage the closure 16 as the dispenser tip 18 is installed onto the dispenser body 12 whereby the closure 16 is moved from the first, sealing position to the second position as the dispenser tip 18 is attached to the dispenser body 12. In this manner, the dispenser 10 is placed in condition to dispense the first and second components 28, 30 of the dental impression material when the dispenser tip 18 is attached to the dispenser body 12. Accordingly, after the dispenser tip 18 has been attached to the body 12, the first and second plungers 50, 52 of the actuator 14 may be urged into the first and second chambers 20, 22 to dispense the first and second components 28, 30 of the dental impression material through the first and second orifices 32, 34 and through the dispenser tip 18. In one exemplary embodiment, the dispenser tip 18 may further include a mixing element 100 provided within the nozzle 84 and having a series of vanes 102 which are configured to mix the first and second components 28, 30 prior to dispensing from the nozzle outlet 86.

In the preferred embodiment of the invention, the first and second components 28, 30 of the dental impression material comprise silicone compositions forming a base material 28 and a catalyst material 30, respectively. The base and catalyst materials 28, 30 have viscosities of approximately 1 Pa-s to approximately 200 Pa-s, and preferably approximately 10 Pa-s to 100 Pa-s. Unless otherwise indicated, these and other viscosity values described herein represent the viscosity at a shear stress of 100 Pa. The base and catalyst materials 28, 30 are stored in the respective first and second chambers 20, 22, as described above, until it is desired to combine the materials to form the dental impression material. At such time, the base and catalyst materials 28, 30 may be dispensed from their respective chambers 20, 22 and combined by the mixing element 100 in the dispenser tip 18 to produce a desirable dental impression material, commonly referred to as a Type II or Type III dental impression material. In an exemplary embodiment, the viscosity of the dental impression material resulting from the combination of the base and catalyst materials is approximately 20 Pa-s to 2,000 Pa-s, and preferably between approximately 40 Pa-s and 1,000 Pa-s. Advantageously, the dental impression material may be applied directly to the dental anatomy of a patient and/or to a dental tray. In one exemplary embodiment, the dental impression material is thixotropic, whereby it readily flows from the dispenser and onto the patient's dental anatomy while being actuated by the plungers of the dispenser. Accordingly, the material takes the form of the patient's dental anatomy upon being dispensed from the dispensing tip, yet readily forms an impression which does not leak from the dental anatomy into other portions of the patient's mouth.

Preferably, the dental impression material has a yield stress of approximately 0.5 Pa to approximately 100 Pa whereby the material may be easily mixed in a small static mixer, such as provided by the dispenser tip 18 of the present invention. The ability to mix the materials in a small static mixer provides an advantage of minimizing waste of the dental impression materials.

Preferably, the base and catalyst materials, which are combined to form the dental impression material, may be provided in a ratio of 1:1. Advantageously, the 1:1 ratio of base and catalyst materials may be easily provided in the dispenser described above in unit dose quantities.

The following examples illustrate various preferred impression materials useful in practicing the present invention. Neither these examples nor any of the foregoing disclosures should be construed as limiting in any way the scope of the present invention. Unless otherwise indicated, all parts and percentages are by weight.

EXAMPLE 1

A two-component light body impression material having catalyst paste and base paste components is prepared by mixing the ingredients of each component separately in a planetary mixer under vacuum. The resulting pastes may be milled in a three-roller mill to achieve final homogeneity. The composition of each component is indicated in the table below.

TABLE 1

|  | Catalyst | Base |
| --- | --- | --- |
| Vinyl terminated polydimethylsiloxanes (4,000 cSt.) | 56.97 | 47 |
| Polymethylhydrosiloxane crosslinker (30 cSt.) | — | 7 |
| Surfactant (Igepal CO-520) | — | 3 |
| Platinum catalyst diluted with vinyl terminated polydimethylsiloxane (1%) | 1 | — |
| 1,3,5,7-tetravinyltetramethylcyclotetrasiloxane | 0.03 | — |
| Finely divided platinum metal on calcium silicate (1%) | 1 | — |
| Pigments | 1 | 2 |
| Silanated silica | 4 | 4 |
| Calcium silicate Wollastonite | 36 | 37 |
| TOTAL | 100 | 100 |

Both catalyst paste and base paste were loaded into the separate chambers of a single-dose dispenser as described above. A static mixer (3.2 mm diameter) equipped with 12 mixing elements was attached and then depressed to unseal the chambers. The catalyst and base pastes were extruded in a 1:1 volume ratio through the static mixer. The mixed parts has a gel time of 4 minutes 8 seconds and a set time of 8 minutes 48 seconds. The catalyst paste has a viscosity of 17 Pa-s at shear stress of 100 Pa. The base paste has a viscosity of 11 Pa-s at shear stress of 100 Pa. The viscosity for mixed catalyst and base pastes is 111 Pa-s at shear stress of 100 Pa.

EXAMPLE 2

A two-component light body impression material having catalyst paste and base paste components with slightly higher viscosity is prepared by mixing the ingredients of each component separately in a planetary mixer under vacuum. The resulting pastes may be milled in a three-roller mill to achieve final homogeneity. The composition of each component is indicated in the table below.

TABLE 2

|  | Catalyst | Base |
| --- | --- | --- |
| Vinyl terminated polydimethylsiloxanes (4,000 cSt.) | 54.47 | 44 |
| Polymethylhydrosiloxane crosslinker (30 cSt.) | — | 7 |
| Surfactant (Igepal CO-520) | — | 3 |
| Platinum catalyst diluted with vinyl terminated polydimethylsiloxane (1%) | 1 | — |
| 1,3,5,7-tetravinyltetramethylcyclotetrasiloxane | 0.03 | — |
| Finely divided platinum metal on calcium silicate (1%) | 1 | — |
| Pigments | 0.5 | 1 |
| Silanated silica | 7 | 7 |
| Calcium silicate Wollastonite | 36 | 38 |
| TOTAL | 100 | 100 |

Both catalyst paste and base paste were loaded into the separate chambers of a single-dose dispenser as described above. A static mixer (3.2 mm diameter) equipped with 12 mixing elements was attached and then depressed to unseal the chambers. The catalyst and base pastes were extruded in a 1:1 volume ratio through the static mixer. The mixed paste has gel time of 5 minutes 19 seconds and a set time of 11 minutes 21 seconds. The catalyst paste has a viscosity of 27 Pa-s at shear stress of 100 Pa. The base paste has a viscosity of 17 Pa-s at shear stress of 100 Pa. The viscosity for mixed catalyst and base pastes is 182 Pa-s at shear stress of 100 Pa.

EXAMPLE 3

A two-component light body impression material having catalyst paste and base paste components is prepared by mixing the ingredients of each component separately in a planetary mixer under vacuum. The resulting pastes may be milled in a three-roller mill to achieve final homogeneity. The composition of each component is indicated in the table below.

TABLE 3

|  | Catalyst | Base |
| --- | --- | --- |
| Blend of vinyl terminated polydimethylsiloxanes (200~60,000 cSt.) | 79.37 | 66.7 |
| Polymethylhydrosiloxane crosslinker (30 cSt.) | — | 8 |
| Polymerizable hydrophilic modifier (SLM 26616) | — | 5 |
| Surfactant (Igepal CO-520) | — | 1.5 |
| Platinum catalyst diluted with vinyl terminated polydimethylsiloxane (1%) | 1.5 | — |
| 1,3,5,7-tetravinyltetramethylcyclotetrasiloxane | 0.03 | — |
| Finely divided platinum metal on calcium silicate (1%) | 0.5 | — |
| Pigments | 0.2 | 0.4 |
| Silanated silica | 10 | 10 |
| Calcium silicate Wollastonite | 8.4 | 8.4 |
| TOTAL | 100 | 100 |

Both catalyst paste and base paste were loaded into the separate chambers of a single-dose dispenser as described above. A static mixer (3.2 mm diameter) equipped with 12 mixing elements was attached and then depressed to unseal the chambers. The catalyst and base pastes were extruded in a 1:1 volume ratio through the static mixer. The mixed paste has a gel time of 1 minute 58 seconds and a set time of 4 minutes 40 seconds. The catalyst paste has a viscosity of 14 Pa-s at shear stress of 100 Pa. The base paste has a viscosity of 25 Pa-s at shear stress of 100 Pa. The viscosity for mixed catalyst and base pastes is 143 Pa-s at shear stress of 100 Pa.

EXAMPLE 4

A two-component medium body impression material having catalyst paste and base paste components is prepared by mixing the ingredients of each component separately in a planetary mixer under vacuum. The resulting pastes may be milled in a three-roller mill to achieve final homogeneity. The composition of each component is indicated in the table below.

TABLE 4

|  | Catalyst | Base |
| --- | --- | --- |
| Blend of vinyl terminated polydimethylsiloxanes (200~60,000 cSt.) | 70.17 | 60.5 |
| Polymethylhydrosiloxane crosslinker (30 cSt.) | — | 8 |
| Polymerizable hydrophilic modifier (SLM 26616) | — | 5 |
| Surfactant (Igepal CO-520) | — | 1.5 |
| Platinum catalyst diluted with vinyl terminated polydimethylsiloxane (1%) | 1.5 | — |
| 1,3,5,7-tetravinyltetramethylcyclotetrasiloxane | 0.03 | — |
| Finely divided platinum metal on calcium silicate (1%) | 0.5 | — |
| Pigments | 0.3 | 0.5 |

TABLE 4-continued

|  | Catalyst | Base |
|---|---|---|
| Silanated silica | 16 | 16 |
| Calcium silicate Wollastonite | 11.5 | 8.5 |
| TOTAL | 100 | 100 |

Both catalyst paste and base paste were loaded into the separate chambers of a single-dose dispenser as described above. A static mixer (3.2 mm diameter) equipped with 12 mixing elements was attached and then depressed to unseal the chambers. The catalyst and base pastes were extruded in a 1:1 volume ratio through the static mixer. The mixed paste has a gel time of 2 minutes 32 seconds and a set time of 5 minutes 31 seconds. The catalyst paste has a viscosity of 49 Pa-s at shear stress of 100 Pa. The base paste has a viscosity of 190 Pa-s at shear stress of 100 Pa. The viscosity for mixed catalyst and base pastes is 748 Pa-s at shear stress of 100 Pa.

While the present invention has been illustrated by the description of the various embodiments thereof, and while the embodiments have been described in considerable detail, it is not intended to restrict or in any way limit the scope of the appended claims to such detail. Additional advantages and modifications will readily appear to those skilled in the art. The invention in its broader aspects is therefore not limited to the specific details, representative apparatus and methods and illustrative examples shown and described. Accordingly, departures may be made from such details without departing from the scope or spirit of Applicant's general inventive concept.

What is claimed is:

1. A delivery system for supplying a single-dose quantity of a two-component dental impression material, comprising:
   a dispenser having first and second chambers sized to contain first and second components of the single-dose of dental impression material, respectively;
   a base material disposed in said first chamber, said base material having a viscosity of approximately 1 Pa-s to approximately 200 Pa-s at a shear stress of 100 Pa; and
   a catalyst material disposed in said second chamber, said catalyst material having a viscosity of approximately 1 Pa-s to approximately 200 Pa-s at a sheer stress of 100 Pa.

2. The delivery system of claim 1, wherein said base material and said catalyst material are provided in a ratio of 1:1.

3. The delivery system of claim 1, wherein said base material has a viscosity of approximately 10 Pa-s to approximately 100 Pa-s at a shear stress of 100 Pa.

4. The delivery system of claim 1, wherein said catalyst material has a viscosity of approximately 10 Pa-s to approximately 100 Pa-s at a shear stress of 100 Pa.

5. The delivery system of claim 1, wherein the dental impression material resulting from the combination of said base material and said catalyst material has a viscosity of approximately 20 Pa-s to approximately 2,000 Pa-s at a shear stress of 100 Pa.

6. The delivery system of claim 5, wherein the dental impression material resulting from the combination of said base material and said catalyst material has a viscosity of approximately 40 Pa-s to approximately 1,000 Pa-s at a shear stress of 100 Pa.

7. The delivery system of claim 1, wherein the dental impression material resulting from the combination of said base material and said catalyst material has a yield stress of approximately 0.5 Pa to approximately 100 Pa.

8. The delivery system of claim 1, wherein the dental impression material resulting from the combination of said base material and said catalyst material is thixotropic.

9. A delivery system for supplying a single-dose quantity of a two-component dental impression material, comprising:
   a dispenser body having first and second adjacent chambers sized to contain first and second components of the single dose of dental impression material, said first and second chambers having first and second dispensing orifices proximate first ends of said chambers and having first and second openings proximate second ends of said chambers;
   first and second components of the single dose of dental impression material disposed within said first and second chambers, respectively;
   said first component comprising a base material having a viscosity of approximately 1 Pa-s to approximately 200 Pa-s at a shear stress of 100 Pa;
   said second component comprising a catalyst materiel having a viscosity of approximately 1 Pa-s to approximately 200 Pa-s at a shear stress of 100 Pa;
   first and second plungers disposed in said first and second chambers, respectively, through said first and second openings, and configured for movement therein to discharge said first and second components through said first and second dispensing orifices;
   a closure having first and second sealing members sealingly engageable with said first and second dispensing orifices, respectively, to seal said first and second chambers, respectively, said closure movable between a first position wherein said first and second sealing members seal said first and second orifices to thereby seal said first and second chambers and a second position wherein said first and second sealing members are moved out of engagement with said orifices to permit said first and second components to be dispensed from said orifices by movement of said plungers; and
   a dispensing tip attachable to said dispenser body and having an input end proximate said first and second orifices when said dispensing tip is attached to said dispenser body, said input end configured to receive said first and second components of said dental impression material from said first and second orifices, said dispensing tip having an output end through which said first and second components of said dental impression material input to said dispensing tip are output for application to a desired target.

10. The delivery system of claim 9, further comprising:
    a movable actuator coupled to said plungers to simultaneously advance said plungers to simultaneously discharge said first and second components through said first and second dispensing orifices.

11. The delivery system of claim 10, wherein said first and second chambers have substantially equal volumes and transverse cross-sections, and wherein said first and second plungers have transverse cross-sections approximating the transverse cross-section of their respectively associated chambers, for simultaneously dispensing said first and second components through said first and second dispensing orifices at substantially equal volume flow rates.

12. A method of forming a dental impression, comprising:
    obtaining a single dose quantity of a two-component dental impression material in a delivery system comprising:

a dispenser having first and second adjacent chambers sized to contain first and second components of the single dose of dental impression material, respectively, a base material disposed in said first chamber, said base material having a viscosity of approximately 1 Pa-s to approximately 200 Pa-s at a shear stress of 100 Pa, and a catalyst material disposed in said first chamber, said catalyst material having a viscosity of approximately 1 Pa-s to approximately 200 Pa-s at a shear stress of 100 Pa;

dispensing said first and second components of the single dose of dental impression material;

mixing said first and second components of the single dose of dental impression material through a dispensing tip containing mixing vanes; and applying the mixed impression material to the dental anatomy of a patient.

13. The method of claim 12, further comprising:

applying the mixed impression material to a dental tray.

14. The method of claim 12, further comprising:

mixing the base and catalyst material as it is dispensed from the dispenser.

* * * * *